US009029109B2

(12) United States Patent
Hur et al.

(10) Patent No.: US 9,029,109 B2
(45) Date of Patent: May 12, 2015

(54) MICROFLUIDIC VORTEX-ASSISTED ELECTROPORATION SYSTEM AND METHOD

(71) Applicant: President and Fellows of Harvard College, Cambridge, MA (US)

(72) Inventors: Soojung Claire Hur, Cambridge, MA (US); Hoyoung Yun, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/961,084

(22) Filed: Aug. 7, 2013

(65) Prior Publication Data

US 2015/0044750 A1   Feb. 12, 2015

(51) Int. Cl.
    *C12N 15/87*   (2006.01)
    *C12N 15/85*   (2006.01)
    *C12N 13/00*   (2006.01)

(52) U.S. Cl.
    CPC ..................... *C12N 13/00* (2013.01)

(58) Field of Classification Search
    CPC ............. B01L 2400/04; B01L 2400/0415;
        B01L 2400/0421; B01L 2400/0424; B01L
        2300/00; B01L 2300/08; B01L 2300/0861;
        B01L 2300/0867; A61N 1/18; A61N 1/205;
        A61N 1/32; A61N 1/327; C12N 13/00
    See application file for complete search history.

(56) References Cited

U.S. PATENT DOCUMENTS

| 6,074,605 A | 6/2000 | Meserol et al. |
| 7,473,361 B2 | 1/2009 | Craighead et al. |
| 2011/0189650 A1 | 8/2011 | Ayliffe et al. |
| 2013/0171628 A1 | 7/2013 | Di Carlo et al. |

FOREIGN PATENT DOCUMENTS

WO   WO-2011/142813 A1   11/2011

OTHER PUBLICATIONS

Wang, J. et al. 2010. Vortex-assisted DNA delivery. Lab on a Chip 10: 2057-2061. specif. pp. 2057-2059.*
Lieu, V.H. et al. 2012. Hydrodynamic tweezers: Impact of design geometry on flow and microparticle trapping. Analytical Chemistry 84: 1963-1968. specif. pp. 1963-1964, 1967-1968.*
Valero, A. et al. 2008. Gene transfer and protein dynamics in stem cells using single cell electroporation in a microfluidic device. Lab on a Chip 8: 62-67. specif. 62-63.*
Herling, T.W., et al., "Integration and characterization of solid wall electrodes in microfluidic devices fabricated in a single photolithography step", Department of Physiology, Development and Neuroscience, University of Cambridge, Downing Street, Cambridge CB2 3DY, United Kingdom (Dated: May 16, 2013), (May 16, 2013), 1-5.

(Continued)

*Primary Examiner* — John S Brusca
*Assistant Examiner* — Sharon M Papciak
(74) *Attorney, Agent, or Firm* — Schwegman Lundberg & Woessner, P.A.

(57) ABSTRACT

A system and method include delivering cells of interest to multiple traps via a channel connecting the traps, maintaining a vortex flow in the traps to trap the cells of interest in the traps, providing first molecules of interest to the traps, and providing an electric field across the traps to perform electroporation of the first molecules of interest into the cells of interest in the traps.

21 Claims, 4 Drawing Sheets

(56) References Cited

OTHER PUBLICATIONS

Sciambi, Adam, et al., "Generating Electric Fields in PDMS Microfluidic Devices With Salt Water Electrodes", (Mar. 17, 2014), 5 pgs.

"International Application Serial No. PCT/US2014/050137, Invitation to Pay Additional Fees and Partial Search Report mailed Nov. 20, 2014", 3 pgs.

Yun, et al., "Sequential multi-molecule delivery using vortex assisted electroporation", Lab Chip 2013, 13, 2764, [Online]. Retrieved from the Internet: <URL:http://pubs.rsc.org/en/content/arflctetanding/2013/ic/c3lc50196e#ldlv>, (Apr. 25, 2013), 15 pgs.

"International Application Serial No. PCT/US2014/050137, International Search Report mailed Jan. 23, 2015", 4 pgs.

"International Application Serial No. PCT/US2014/050137, Written Opinion mailed Jan. 23, 2015", 5 pgs.

\* cited by examiner

MICROFLUIDIC VORTEX-ASSISTED ELECTROPORATION SYSTEM AND METHOD

BACKGROUND

The ability to introduce foreign molecules into living cells and human tissues has significant implications for various applications in biological research and medicine. Numerous methods including virus-mediated, chemical, physical, and optical approaches have been developed in order to deliver exogenous molecules into the cells. Currently, virus-mediated approach is the most efficient way of gene delivery and expression; however, besides being capable only for delivery of nucleic acids, there are considerable risks accompanied with viral delivery systems, including toxicity, chromosomal integration and immunogenicity. Viral approaches are, hence, less than ideal for many clinical and research applications, which require minimal post transplantation risks, such as gene therapies and studies of cellular reprogramming or lineage conversions.

Consequently, non-viral molecular delivery techniques have begun to gain more attention as inevitable alternatives. Among these techniques, electroporation is considered as an effective and powerful technique because of its ability to introduce countless types of molecules into target cells both in vitro and in vivo without need for potentially cell-damaging chemical reagents or viruses. Electroporation utilizes short high-voltage pulses to transiently and reversibly create pores on cell membrane through which molecular probes of interest can be delivered into the cytosol. However, conventional electroporation techniques using cuvettes or microcapillaries rely on bulk stochastic molecule delivery processes, making those systems ill-suited for applications requiring precisely and individually controlled transferred molecular doses. Moreover, it is difficult to obtain practical efficiency and viability for samples with large heterogeneity in cell diameter since the electric field strength required to transiently disrupt cellular membrane strongly correlate with the cell size.

Recent advances in microfluidics facilitated development of microscale electroporation techniques, allowing the single-cell level electroporation and dosage control of transferred molecules with enhanced cell viability. Despite their noteworthy improvement in throughput and molecular delivery efficiency with enhanced viability, a single-directional flow-through scheme under which most of current microfluidic electroporation systems operate renders current microfluidic electroporators do not provide for multiple different molecules and also lack good dosage control.

SUMMARY

A system and method include delivering cells of interest to multiple traps via a channel connecting the traps, maintaining a vortex flow in the traps to trap the cells of interest in the traps, providing first molecules of interest to the traps, and providing an electric field across the traps to perform electroporation of the first molecules of interest into the cells of interest in the traps.

In one device, a first channel has an inertial focusing region to move cells in a solution travelling through the first channel towards sides of the channel. A plurality of serial opposed pairs of traps are disposed along a length of the first channel downstream of the inertial focusing region. The size of each trap is adapted to promote vortex flow within the traps while the solution is flowing through the first channel to trap the cells in the traps. An outlet of the channel is provided downstream from the plurality of serial opposed pairs of traps. Electrodes are coupled to ends of the opposed traps to apply an electric field across the traps suitable for eletroporation of molecules into the cells.

DETAILED DESCRIPTION

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

The functions or algorithms described herein may be implemented in software or a combination of software and human implemented procedures in one embodiment. The software may consist of computer executable instructions stored on computer readable media such as memory or other type of storage devices. Further, such functions correspond to modules, which are software, hardware, firmware or any combination thereof. Multiple functions may be performed in one or more modules as desired, and the embodiments described are merely examples. The software may be executed on a digital signal processor, ASIC, microprocessor, or other type of processor operating on a computer system, such as a personal computer, server or other computer system.

In various embodiments, a system and method provide vortex-assisted microfluidic electroporation utilizing sequential multi-molecule delivery to pre-selected target cells with precise and independent molecular amount and parameter controllability.

Figure 1:
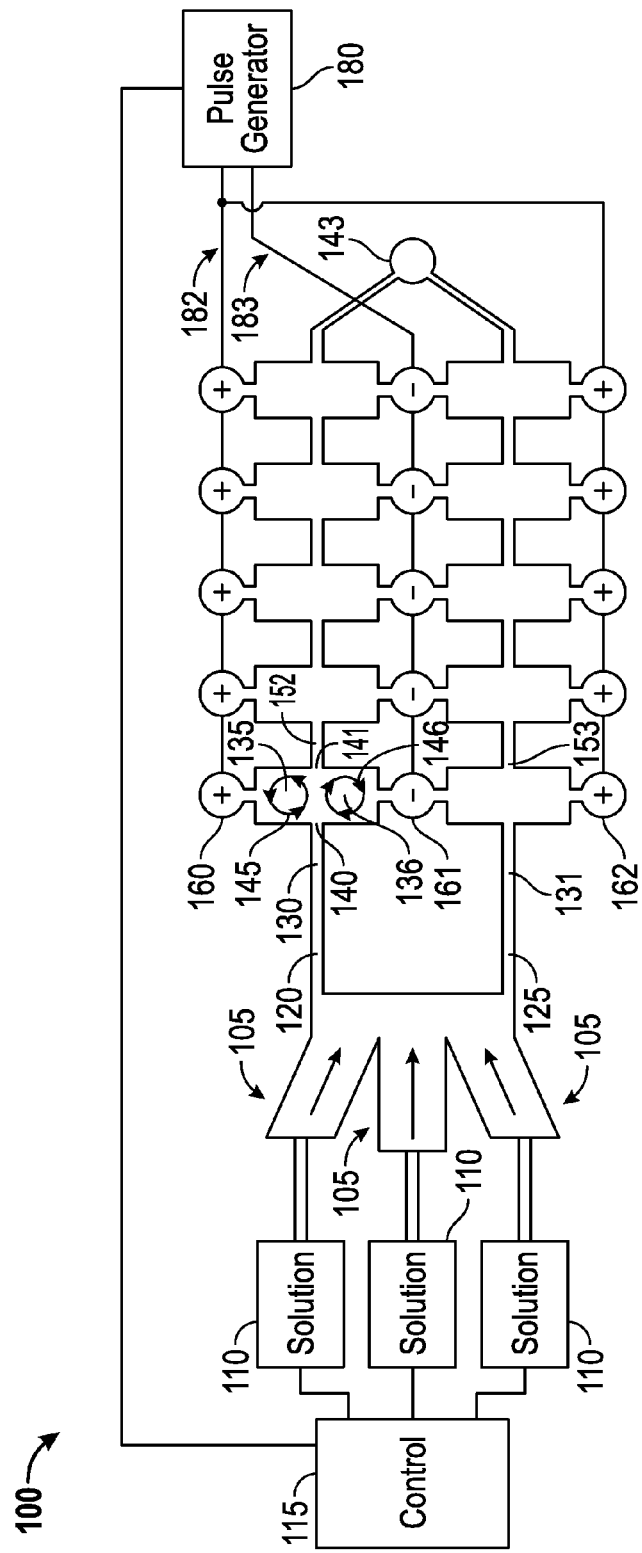
FIG. 1 is a block diagram top view of an electroporation system according to an example embodiment.

FIG. 1 illustrates an electroporation system generally at 100 in one embodiment. System 100 in one embodiment includes multiple inlets 105 coupled to receive solution from multiple sources of solution 110. In various embodiments, the sources 110 are suitable for holding a solution that includes cells of interest, and various solutions containing different molecules of interest. In some embodiments, the solutions may also include solutions for incubation and washing or flushing (such as DPBS) between or after flows of the various solutions. A controller 115 controls the sources 110 to sequentially supply the solutions in a desired manner to the input ports. In one embodiment, the controller comprises a pneumatic flow control system that timely and independently pressurizes individual solution chambers 110 to drive flow through the microfluidic electroporator 100. The controller also controls valves, such as a valve manifold to provide the various solutions in a controlled sequential manner.

The inlets 105 may include coarse filters and are each coupled to at least a first channel 120, and optionally a second channel 125 to provide the solutions to the channels. The first and second channels run substantially parallel to each other in one embodiment and receive the same solutions. Further channels may be included in further embodiments. Each channel may also include an inertial focusing region illustrated at 130, 131 respectively. The inertial focusing regions serve to allow migration responsive to fluid dynamic forces of cells in solution toward walls of the channels.

Multiple chambers, referred to as traps 135, 136 and 138, 138 for example are coupled to the channels 120 and 125 respectively, downstream from the inertial focusing regions 130, 131. In one embodiment, each channel as several pairs of opposing traps that are disposed about a trap entrance 140 and trap exit 141 in each pair of traps. The entrance 140 and exit 141 effectively bisect the pair of traps 135, 136, which form a rectangular structure. The solutions continue to run through the pair of traps via respective inlets and outlets of each pair, and finally exits one or more channel outlets represented at outlet 143 where waste and cells may be collected.

In the embodiment shown, there are ten traps per channel corresponding to five pairs of opposing traps. Given two channels, that makes for 20 total traps. In further embodiments, up to 80 or more pairs of traps may be formed, equating to 160 or more vortices for trapping cells. The traps and channels may be formed of a polydimethly siloxane (PDMS) sheet in one embodiment from a silicon casting mold formed using common photolithographic processes. The PDMS sheet may be activated (or functionalized), such as by an oxygen plasma cleaner and topped with a glass sheet to enclose the traps and channels. In further embodiments, different materials may be used, allowing higher pressures and hence additional pairs of traps.

The sizes of the traps in one embodiment are selected such that the solution flowing through the channel and traps forms a vortex in each trap as illustrated for example at 145 in trap 135 and at 146 in trap 136. The cells are trapped in the vortices 145, 146 while the solution is flowing when the Reynolds number is greater than approximately 100. The solution keeps flowing through each of the remaining opposed trap pairs separated by sections 152, 153 of the channels. Each trap pair has vortices created, along with trapped cells as the solution flows toward the outlet 143. In one embodiment, each of the traps may contain almost identical populations of cells.

In some embodiments, the forces acting on the cells may cause the cells to be inertially focused to distinct lateral equilibrium positions near the channel walls, such as in inertial focusing regions 130, 131 depending on their biophysical properties (e.g., size and deformability). This particle/cell ordering phenomenon could be resulted from a balance between two counteracting inertial lift forces, namely a wall effect lift and a shear-gradient lift, acting on flowing cells. As inertially focused flowing cells enter the suddenly-expanding traps, also referred to as a electroporation chamber regions, the shear-gradient lift alone induces lateral migration of flowing cells towards the core of microscale vortex since the magnitude of the wall effect lift that had entrained cells at the distinct lateral positions in the straight focusing channel diminishes due to disappearance of channel walls from the vicinity of flowing cells. Since the shear-gradient lift force scales with the third-power of cell's diameter, larger cells are prone to migrate much more rapidly toward the vortex core than smaller cells are. Once larger cells migrate close enough to vortices, they remain trapped in the vortices while smaller cells were being flushed out of the device. This gentle and stable cell trapping mechanism allows cascading additional biological assays in situ. The sample injection time may be varied from 20 to 30 seconds at a fixed flow rate of 400 μL/min in order to investigate time-dependent variations in size and number of trapped cells in the electroporation chambers. Further variation of the parameters may occur in further embodiments.

Once a desired number of cells are trapped in the traps by the vortices, the cell solution may be flushed. An optional flushing solution may be used to flush the cell containing solution, followed by a new solution containing molecules of interest. The flow of solutions may be maintained to maintain the vortices and keep the cells trapped in the traps. The cell containing solution is effectively removed from the traps and channels by the new solution. Once a desired concentration of molecules of interest is obtained about the cells in the traps, electrodes 160, 161, 162 are used to create an electric field across the traps, and cause the molecules of interest to transfer the molecules into the cells. Inherently membrane-impermeant molecules can be transferred uniformly across an entire cytosol with a precisely controlled amount.

In one embodiment, electrodes may be coupled to electrical equipment 180 for generating high-voltage short-pulses in the electroporation chambers. The equipment 180 in one embodiment includes a pulse generator and two electrodes 182, 183 which may be made of platinum or other conductive material. The electrodes 182, 183 may be coupled to electrodes 160, 162, and 161 respectively, which may be directly in contact with a solution in the electroporation traps via ports in the traps. In one embodiment, square wave pulses with magnitude, V, may be varied from 10 V to 200 V to provide an electric field strength, $E=V/L_e$, applied across the electroporation traps or chambers ranging from 0.1 to 2 kV/cm. The magnitude and duration of applied pulses may be varied simultaneously in order to determine the optimum electrical condition for sequential multi-molecule delivery.

In further embodiments, further solutions with different molecules may be sequentially delivered and optionally transferred into the cells via electrode initiated electroporation. In one embodiment, the electrodes are disposed about ends of the traps in an efficient manner, with traps from different channels that are adjacent to each other sharing a common electrode of a selected polarity, such as negative polarity as shown at 161. Electrodes 160 and 162 are shown as opposite polarity, in this case positive.

The channels and traps in the figures are not necessarily shown to scale. Some example dimensions include the channel having a width such that cells traveling through the channel are approximately 30 percent or greater than the width of the channel. For example, breast cancer cells may be 16-20 μm in diameter, resulting in a 40 to 50 μm size channel. The cancer cells in one embodiment may be buffered in a phosphate buffered saline solution such as DBPS, 1×, without $Ca^{2+}$ and $Mg^{2+}$, Cellgro®, Mediatech, USA with a concentration ranging from $1 \times 10^5$ to $1 \times 10^6$ cells/ml. Cell concentration may be varied significantly in further embodiments. The inertial focusing regions may be approximately 0.7 cm or longer in some embodiments to ensure migration of the cells toward walls that facilitate entry of the cells into the vortices. In one embodiment, the traps may have sides of between approximately 1 mm to 500 μm, and are approximately square in cross section. In further embodiments, the side of the trap running with the channel may be longer than the distance or depth that the trap extends away from the channel.

In one example embodiment, the inertial focusing channel may have dimensions of (L=4.5 cm, W=40 μm, and H=60

μm). The electroporation chambers or traps have an approximately square shape with each edge, $W_c=400$ μm. The dimensions may be varied in further embodiments, with a length of the traps along the length of the channel being longer than the width while still maintaining the ability to maintain a vortex flow in the traps via the solutions. The height of the traps may be substantially the same as the height of the channel to maintain ease of manufacturing. The height may vary in further embodiments.

In one embodiment, the structure described is able to trap breast cancer cells in the traps, and a further solution containing propidium iodide may be delivered to the trapped cells. Further molecules having a wide range of molecular weights such as Dextran (3,000 to 70,000 Da, neutral or anionic molecules) may be delivered to the trapped cells in further embodiments. The cells and different molecules may be delivered sequentially, such that for each molecule, the electric field may be tailored for electroporation of each cell and molecule combination. In addition, a broad range of molecules commonly used in biological applications may be used. In some embodiments, a broad range of molecules, regardless of their electrical charges (e.g., anionic or neutral) can be introduced into the cells using identical electrical parameters.

In one embodiment, system 100 may be an on-chip microscale electroporation system that enables sequential delivery of multiple molecules with precise and independent dosage controllability into pre-selected nearly identical populations of target cells. The system 100 provides the ability to trap cells with uniform size distribution contributing to enhanced molecular delivery efficiency and cell viability. Additionally, the system 100 may provide real-time monitoring ability of the entire delivery process, allowing timely and independent modification of cell- and molecule-specific electroporation parameters. A precisely controlled amount of inherently membrane-impermeant molecules may be transferred into cells, such as human cancer cells, by varying electric field strengths and molecule injection durations.

In one embodiment, fluidic forces tend to push larger particles, such as cells and larger molecules outward from the direction of flow and cause them to be more likely to be trapped in the vortices than smaller particles. Smaller particles are also less likely to be trapped even if they enter the vortices, making it effective to flush out solutions used to carry the larger particles once trapping and electroporation have been performed.

Figure 2:
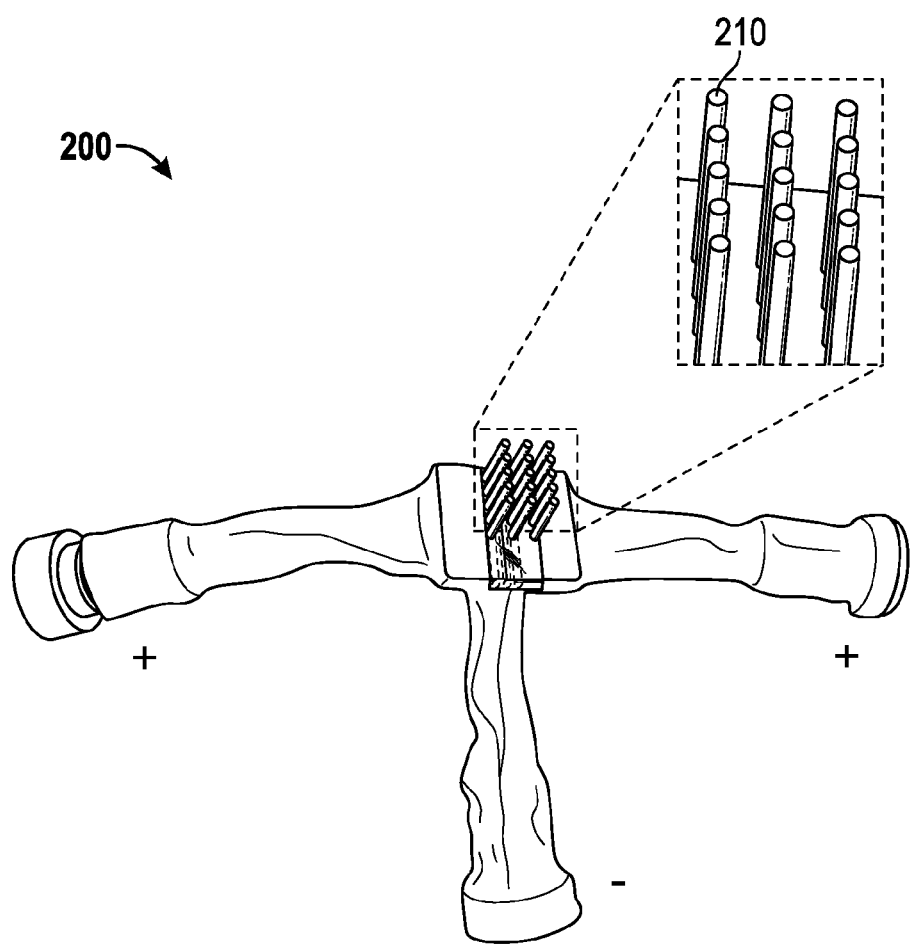
FIG. 2 is a perspective view of an electrode used to create a substantially uniform electric field across traps according to an example embodiment.

FIG. 2 is a perspective view of an electrode 200 used to create a substantially uniform electric field across the traps. In one embodiment, the electrodes 200 are formed with multiple projections 210 in the shape of pins, generally round cylinders, or other shapes. The electrodes may be formed of aluminum in one embodiment, and may consist of fifteen or so projections formed in an array, such as a 3×5 array mounted in an acrylic with pre drilled holes. Other mounting materials and methods may be used to create a seal between the electrodes and the traps, and may result in smaller electrodes. Smaller electrodes may be used to decrease spacing along the channels between traps, resulting in a higher density and larger number of traps. In further embodiments, the electrodes may be formed of other conductive material and formed with more uniformly spaced projection about an area corresponding to the area of the traps in order to provide a more uniform electric field to ensure generally the same electroporation results for each cell trapped in the traps. The electrodes may be positioned to communicate with the solution in the trap without projecting into the trap in a manner that might be adverse to formation and maintenance of the vortices.

In one example method, each solution may be injected into the device sequentially at an operating pressure of 40 psi (equivalent to a flow rate of 400 μL/min) using the flow control 115. Prior to the cell solution injection, the washing solution may be injected for >1 min in order to prime the flow speed required for stable microscale vortex generation. Then, target cells are isolated into the electroporation chambers using the microvortex trapping mechanism simply by switching the active solution port from the washing solution to the cell solution.

Once the desired size and number distribution of trapped cells has been achieved, solution is rapidly exchanged to the washing solution in order to remove non-trapped contaminating cells from the entire device without disturbing orbits that trapped cells created. After the device is flushed for 20 s, solutions containing the first and the second molecule to be transferred (e.g., fluorescent nucleic dyes or fluorescent protein plasmids) may be sequentially injected.

Single or multiple short pulses of high electric field may be applied promptly after injection of each molecular solution had been initiated. The magnitude, duration and number of square pulses as well as incubation time could be individually varied depending on cellular and molecular types to have better experimental outcomes. Upon completion of molecular delivery using electroporation, the processed cells may be re-suspended in the washing solution and released from the device for downstream analysis by simply lowering the operating pressure to below 5 psi, followed by final device flushing step at 40 psi for 10 s.

The average size and size-uniformity of the captured cells in the electroporation chambers increases with increasing cell solution injection time. While the average diameter of trapped cells, $D_{ave}$, may be about 20 μm with a coefficient of variation (CV) of 40% shortly after the cell solution injection has been initiated (t=10 s), the $D_{ave}$ may increase to 32 μm with a reduced CV of 25% at t=30 s. For a square electroporation chamber geometry (Each side=400 μm), the average number of cells processed in each run may be about 20 when the maximum size and uniformity have been achieved and the number of cells is maintained identical throughout the course of the entire electroporation processes.

The ability to trap cells with a uniform size distribution positively contributes to having better molecular delivery efficiency and cell viability because the cell size distribution has significant implication for membrane permeabilization. When cells are exposed to an extracellular electric field, E, transmembrane potential, $\Delta V_m = f E D \cos \theta$, is induced in a cell. Here, f is the weighting factor, which is the measure of how cells contribute on the applied electric field distribution, and D and θ are the cell diameter and the polar angle measured with respect to the external field, respectively. In order to transiently permeabilize cells without cell lysis, $\Delta V_m$ should exceed the transmembrane potential, $\Delta V_s$, but remain below the irreversible electroporation threshold, $\Delta V_c$. For mammalian cells, $\Delta V_s$ is reported to range between 200 mV and 1 V, depending on pulse duration, while $\Delta V_c$ is expected to be greater than 1 V. Previous electroporation tests performed with cell lines that have a large size variation are reported to have low electroporation efficiency and viability since samples with higher heterogeneity in size are expected to have more number of cells having induced $\Delta V_m$ that falls outside of the optimum range for successful transient permeabilization. Therefore, the current system's ability to preisolate cells with higher homogeneity in size may minimize undesirable consequences associated with a large cell size variation.

In one embodiment, the amount of transferred molecule proportionally increases with the electric field strength when cells are exposed to the identical molecular amount (for example, solution injected into the device for 40 s (6.4 µg) and processed cells were washed with molecule-free DPBS for 10 s. An $E_i$=0.4 kV/cm is sufficient in one embodiment to initiate the delivery of molecules to the cells and E exceeding 2.0 kV/cm may result in cell lysis. Similarly, the molecular transfer dosage can be monotonically increased by increasing solution injection time with the set electric field strength, $E_o$=0.8 kV/cm. $E_o$ is one of the optimal conditions, where processed cells exhibited high viability (83%) and electroporation efficiency (70%). Electroporated cells' molecular uptake may be initiated after cells are exposed to approximately 800 ng of molecules (equivalent to the solution injection time, t=5 s). For different cells, similar trends may be observed with slightly higher $E_i$=0.6 kV/cm and $E_o$=1.0 kV/cm. Different effective electric field values may depend on differences in membrane properties or average cell diameter. The system's rapid solution exchange scheme combined with real-time monitoring ability enabled the precisely and independently control and optimization of each transferred molecular dosage simply by varying incubating-duration and/or electric field strength.

Interestingly, molecules uptaken by cells electroporated using the proposed vortex-assisted system may be distributed uniformly across entire cytosol while cells electroporated in the identical device under the static condition may be partially occupied by delivered molecules. Presumably, gentle and continuous agitation of cells trapped in vortices during the electroporation process that the current system uniquely provides may promote uniform permeabilization, known to be a key factor improving electroporation efficiency. In fact, cells electroporated using the current system may exhibit a three-fold higher electroporation efficiency than that of previous studies utilizing stationary cell samples.

In the case of multi-gene transfection of MDA-MB-231 cells, the results may be comparable to the results obtained from the conventional cuvette system under the identical electroporation condition (E=0.7 kV/cm with pulse width of 30 ms and plasmid concentration of 15 µg/ml). Transfection efficiencies were not significantly different from that of the conventional cuvette system (p>0.1) may mean that reduction in transfection efficiency is presumably caused by difficulties associated with naked plasmid delivery processes and/or potentially reflects the upper limit for tested plasmids used in electroporation.

An exceptionally low operational electric current results in a temperature rise of less than 1° C., whereas the instant temperature rise of the conventional cuvette test calculated to be ΔT=38° C. from Joule heating when the identical operational electrical field is applied (V=160V, Le=2 mm and I=5 A). Expectably, cells electroporated using the system 100 showed a 7-fold higher viability than that observed from cells processed using the conventional cuvette system.

Figure 3:
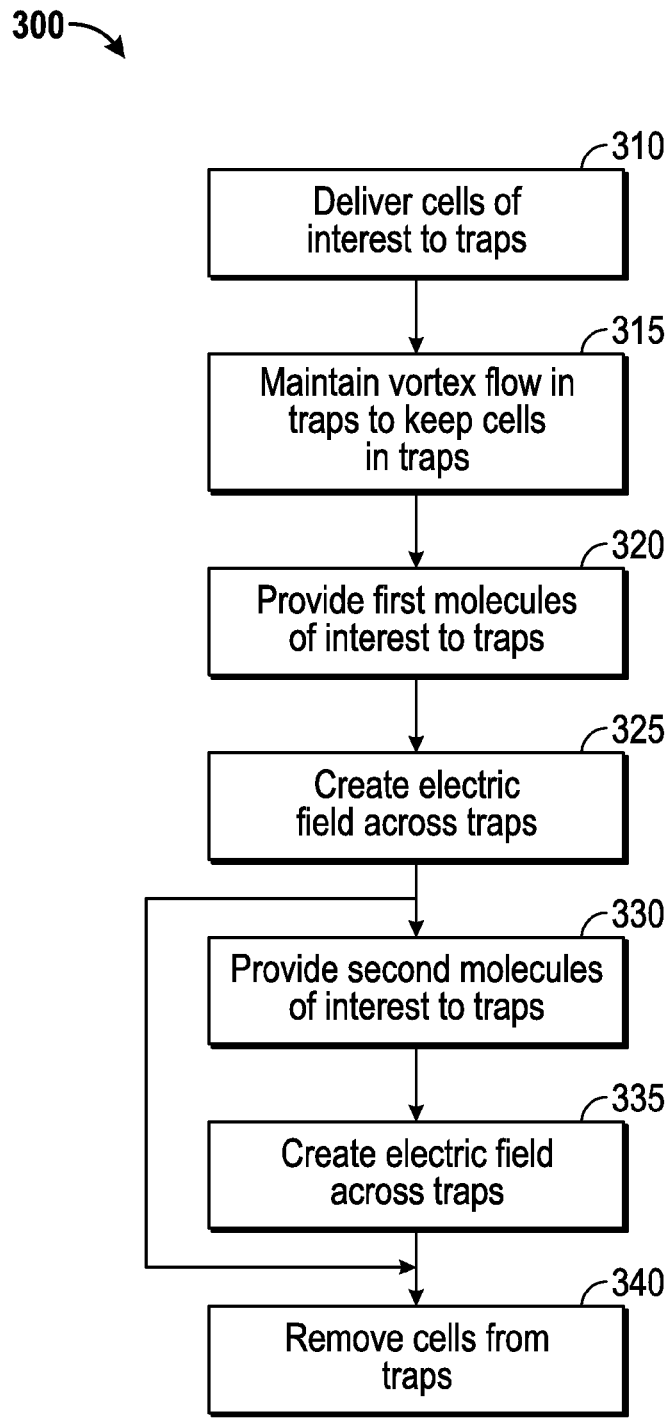
FIG. 3 is a flowchart illustrating a method of trapping cells and performing electroporation according to an example embodiment.

FIG. 3 is a flowchart illustrating a method 300 of trapping cells and performing electroporation according to an example embodiment. Method 300 includes delivering cells of interest to multiple traps via a channel connecting the traps as indicated at 310. At 315, a vortex flow is maintained in the traps to trap the cells of interest in the traps. At 320, first molecules of interest are provided to the traps. Once the cells are trapped in the vortex, an electric field is provided across the traps to perform electroporation 325 of the first molecules of interest into the cells of interest in the traps. In one embodiment, the electric field across the traps is substantially uniform.

In one embodiment, delivering cells of interest at 310 is performed by transporting a first fluid solution containing the cells of interest via the channel at a speed such that the fluid has a Reynolds number of greater than 100 to create the vortex flow in the traps. Providing first molecules of interest to the traps at 320 may include using a second fluid solution containing the molecules of interest while maintaining the vortex flow in the traps and removing the first solution.

In a further embodiment, a third solution containing further molecules of interest is provided at 330 while maintaining the vortex flow in the traps. The further molecules of interest being provided following electroporation of the first molecules of interest. Following provision of the further molecules of interest, an optional electric field is provided at 335 across the traps to perform electroporation of the second molecules of interest into the cells of interest in the traps. The electric field may be applied once to deliver the two different molecules of interest in one embodiment. In further embodiments, the electric field may be adjusted or tailored to optimize delivery of each different molecule, especially if the molecules have quite different molecular sizes or electrical properties. The second fluid is replaced with the third solution while maintaining the vortex flow in the traps. The vortex flow may be maintained during the entire method to keep the cells trapped in the traps. The cells may be removed from the traps as indicated at 340, either following electroporation with the first molecules of interest at 325, or following electroporation with the second molecules of interest at 335.

In a further embodiment, delivering cells of interest in solution to multiple traps via the channel connecting the traps at 310 includes providing the first solution to the channel via an inertial focusing region to cause the cells of interest to move close to the sides of the channel via fluidic forces. In yet a further embodiment, the channel breaks into multiple channels, each having opposing pairs of traps disposed along a length of the channels.

Figure 4:
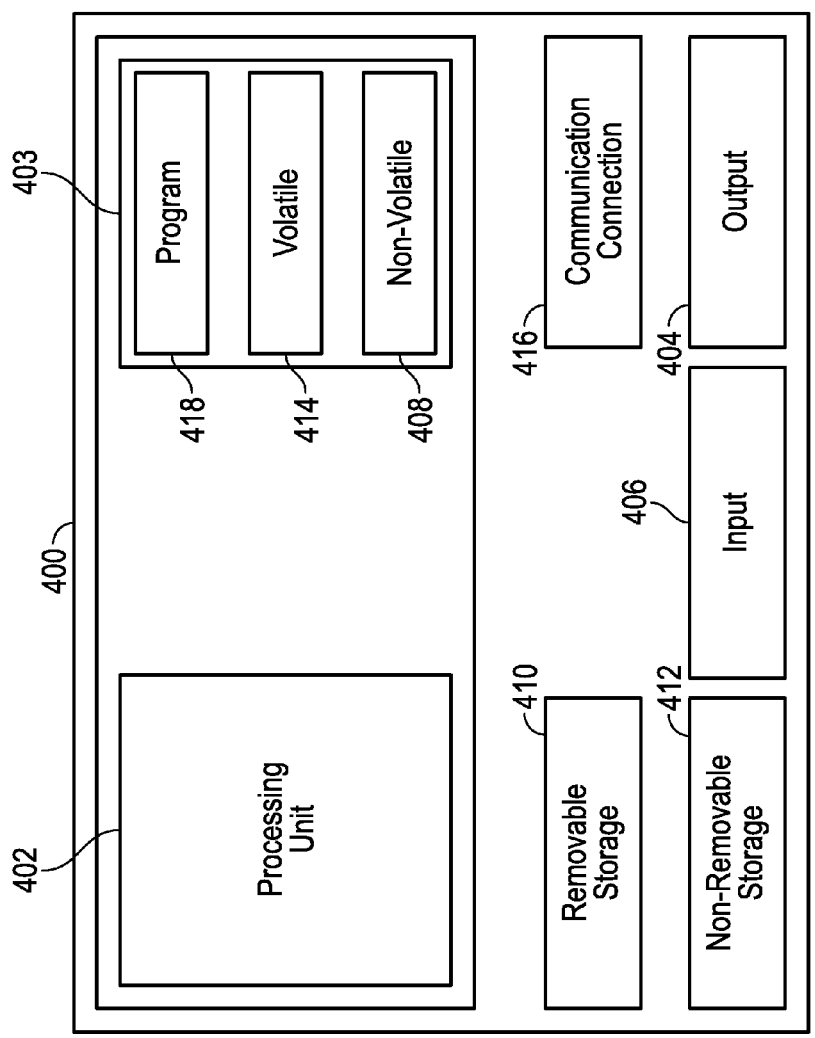
FIG. 4 is a block schematic diagram of a computer system to implement control functions in one or more example embodiments.

FIG. 4 is a block schematic diagram of a computer system 400 to implement control 115 in one or more example embodiments. An object-oriented, service-oriented, or other architecture may be used to implement functions for performing control methods. One example computing device in the form of a computer 400 may include a processing unit 402, memory 403, removable storage 410, and non-removable storage 412. Memory 403 may include volatile memory 414 and non-volatile memory 408. Computer 400 may include—or have access to a computing environment that includes—a variety of computer-readable media, such as volatile memory 414 and non-volatile memory 408, removable storage 410 and non-removable storage 412. Computer storage includes random access memory (RAM), read only memory (ROM), erasable programmable read-only memory (EPROM) & electrically erasable programmable read-only memory (EEPROM), flash memory or other memory technologies, compact disc read-only memory (CD ROM), Digital Versatile Disks (DVD) or other optical disk storage, magnetic cassettes, magnetic tape, magnetic disk storage or other magnetic storage devices, or any other medium capable of storing computer-readable instructions. Computer 400 may include or have access to a computing environment that includes input 406, output 404, and a communication connection 416. The computer may operate in a networked environment using a communication connection to connect to one or more remote computers, such as database servers. The remote computer may include a personal computer (PC), server, router, network PC, a peer device or other common network node, or the like. The communication connection may include a Local Area Network (LAN), a Wide Area Network (WAN) or other networks.

Computer-readable instructions stored on a computer-readable medium are executable by the processing unit 402 of the computer 400. A hard drive, CD-ROM, and RAM are some examples of articles including a non-transitory computer-readable medium. For example, a computer program 418 capable of providing a generic technique to perform access control check for data access and/or for doing an operation on one of the servers in a component object model (COM) based system may be included on a CD-ROM and loaded from the CD-ROM to a hard drive. The computer-readable instructions allow computer 400 to provide generic access controls in a COM based computer network system having multiple users and servers.

Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

The invention claimed is:

1. A method comprising:
    delivering cells of interest to multiple traps via fluid flowing along an axis through a channel connecting the traps;
    maintaining a vortex flow in the traps to trap the cells of interest in the traps, wherein the vortex comprises a rotational flow around an axis perpendicular to axis of flow through the channel;
    providing first molecules of interest to the traps; and
    providing an electric field across the traps to perform electroporation of the first molecules of interest into the cells of interest in the traps.

2. The method of claim 1 wherein delivering cells of interest is performed by transporting a first fluid solution containing the cells of interest via the channel at a speed such that the fluid has a Reynolds number of greater than 100 to create the vortex flow in the traps.

3. The method of claim 2 wherein providing first molecules of interest to the traps comprises using a second fluid solution containing the molecules of interest while maintaining the vortex flow in the traps and removing the first solution.

4. The method of claim 3 wherein the electric field across the traps is substantially uniform.

5. The method of claim 3 and further comprising using a third fluid solution containing further molecules of interest while maintaining the vortex flow in the traps, the further molecules of interest being provided following electroporation of the first molecules of interest.

6. The method of claim 5 and further comprising providing an electric field across the traps to perform electroporation of the second molecules of interest into the cells of interest in the traps, wherein the electric field is adapted to enhance delivery of the second molecules of interest to the cells.

7. The method of claim 6 and further comprising replacing the second fluid with additional fluids containing additional molecules of interest while maintaining the vortex flow in the traps.

8. The method of claim 6 wherein the vortex flow is maintained during the entire method.

9. The method of claim 2 wherein delivering cells of interest in solution to multiple traps via the channel connecting the traps includes providing the first solution to the channel via an inertial focusing region to cause the cells of interest to move close to the sides of the channel via fluidic forces.

10. The method of claim 9 wherein the channel breaks into multiple channels, each having opposing pairs of traps disposed along a length of the channels.

11. A system comprising:
    a first channel having an inertial focusing region to move cells in a solution travelling through the first channel towards sides of the channel;
    a plurality of serial opposed pairs of traps disposed along a length of the first channel downstream of the inertial focusing region, the size of each trap adapted to promote vortex flow within the traps while the solution is flowing through the first channel to trap the cells in the traps;
    an outlet of the channel disposed downstream from the plurality of serial opposed pairs of traps; and
    electrodes coupled to ends of the opposed traps to apply an electric field across the traps suitable for electroporation of molecules into the cells.

12. The system of claim 11 wherein the channel has a width such that cells traveling through the channel are approximately 30 percent or greater than the width of the channel.

13. The system of claim 11 wherein the inertial focusing region of the channel is approximately 0.7 cm or longer.

14. The system of claim 11 wherein a second channel configured the same as the first channel is in parallel with the first channel.

15. The system of claim 14 and further comprising multiple inlets to the first and second channel inertial focusing regions, the inlets adapted to receive solutions from multiple sources including a cell solution and a molecule solution.

16. The system of claim 15 wherein the inlets are adapted to receive further solutions for incubation and flushing.

17. The system of claim 14 wherein the first and second channels each include five opposing pairs of traps serially disposed downstream from the inertial focusing region of each channel.

18. The system of claim 14 wherein each trap is approximately square in shape with each opposed pair of traps forming a rectangle having a channel entrance and exit bisecting the opposed pair of traps.

19. The system of claim 18 wherein the traps have sides of between approximately 1 mm to 500 μm.

20. The system of claim 14 wherein the electrodes comprise multiple electrode tips adapted to create a substantially uniform electric field, and wherein traps from the first channel adjacent traps from the second channel share an electrode of one polarity.

21. A system comprising:
    a first channel having an inertial focusing region to move cells in a solution travelling through the first channel towards sides of the channel;
    a plurality of traps disposed along a length of the first channel downstream of the inertial focusing region, the size of each trap adapted to promote vortex flow within the traps while the solution is flowing through the first channel to trap the cells in the traps;
    an outlet of the channel disposed downstream from the plurality of traps; and
    electrodes coupled to ends of the traps to apply an electric field across the traps suitable for electroporation of molecules into the cells.

* * * * *